United States Patent [19]

Ladner et al.

[11] Patent Number: 5,753,495
[45] Date of Patent: May 19, 1998

[54] PROCESS FOR THE PREPARATION OF (L)-2-CHLOROPROPIONIC ACID AND ITS SALTS USING LIPASE FROM PSEUDOMONAS

[75] Inventors: Wolfgang Ladner, Fussgönheim; Hansjörg Rettenmaier, Grünstadt; Bernhard Zipperer, Dirmstein; Hanspeter Hansen, Ludwigshafen, all of Germany

[73] Assignee: BASF Aktiengesellschaft, Ludwigshafen, Germany

[21] Appl. No.: 596,375

[22] PCT Filed: Aug. 17, 1994

[86] PCT No.: PCT/EP94/02738

§ 371 Date: Feb. 15, 1996

§ 102(e) Date: Feb. 15, 1996

[87] PCT Pub. No.: WO95/06130

PCT Pub. Date: Mar. 2, 1995

[30] Foreign Application Priority Data

Aug. 23, 1993 [DE] Germany .................. 43 28 231.8

[51] Int. Cl.[6] .................................................. C12P 7/52
[52] U.S. Cl. .................... 435/280; 435/141; 435/198
[58] Field of Search ............................ 435/141, 180, 435/195, 196, 198, 280

[56] References Cited

U.S. PATENT DOCUMENTS 4,668,628  5/1987  Dahod et al. ............... 435/135
5,278,054  1/1994  Buchner et al. ............ 435/136

FOREIGN PATENT DOCUMENTS 196 625    10/1986  European Pat. Off. .
257 716    3/1988   European Pat. Off. .
57094295   12/1980  Japan .
61-111699  5/1986   Japan .
62205797   5/1986   Japan .

OTHER PUBLICATIONS

Cambou et al., *App. Biochem. and Biotech.*, vol. 9, 1984, pp. 255–260.

Dahod et al., *Biotech. & Bioeng.*, vol. 30, No. 5, Oct. 5, 1987.

*Primary Examiner*—Irene Marx
*Attorney, Agent, or Firm*—Keil & Weinkauf

[57] ABSTRACT

A process for the preparation of (L)-2-chloropropionic acid and its alkali metal, alkaline earth metal or ammonium salts which comprises hydrolyzing isobutyl L-chloropropionate at a pH of from 4 to 8 in the presence of a lipase from Pseudomonas spec. DSM 8246 and isolating the optically active reaction product from the reaction mixture either directly or after conversion of the salt into the acid in a conventional way, or further reacting it in situ. The optically active products are important intermediates for preparing crop protection agents.

6 Claims, No Drawings

PROCESS FOR THE PREPARATION OF (L)-2-CHLOROPROPIONIC ACID AND ITS SALTS USING LIPASE FROM PSEUDOMONAS

The present invention relates to a novel process for preparing (L)-2-chloropropionic acid and its alkali metal, alkaline earth metal or ammonium salts.

JP 57 094 295, JP 62 205 797, EP-A 196 625, JP 61 111 699 and Appl. Biochem. Biotechnol. 9(3) (1984) 255 disclose the enantio-selective enzymatic cleavage of racemic 2-chloropropionic esters. However, the disadvantage in this case is, besides the maximum possible yield of only 50%, the insufficient enantiomeric purity of the 2-chloropropionates formed.

Furthermore, EP-A 257 716 discloses a continuous process in which methyl D,L-2-bromopropionate is used as racemate and converted in a 2-phase system using *Candida cylindracea* lipase into methyl L-(−)-2-bromopropionate. However, no hydrolysis products are isolated in this process.

Furthermore, S. K. Dahod and P. Sinta-Mangano describe in Biotechnol. Bioeng. 30(8) (1987) 995 the lipase-catalyzed hydrolysis of methyl L-2-chloropropionate in the presence of carbon tetrachloride. However, the disadvantage in this case is, besides the use of a chlorinated solvent, the low yield of about 30% with an enantiomeric purity of only 95%.

In addition, EP-A 511 526 teaches a process for the enzymatic hydrolysis of racemic 2-chloropropionic esters in a 2-phase system which consists of water and of an organic solvent, which is substantially immiscible with water, for the ester. This process is very elaborate because it is necessary several times for the organic phase to be separated off, brought into contact with the hydrolase and recycled again. Since, despite relatively long reaction times, only incomplete conversion takes place and enantiomerically pure products are not obtained, this method is unsuitable for the industrial preparation of (L)-2-chloropropionic acid and its sodium salt.

Sodium (L)-2-chloropropionate and (L)-2-chloropropionic acid have to date been prepared by alkaline hydrolysis of isobutyl (L)-2-chloropropionate. However, this often results in a low-quality product (about 90–95% enantiomeric excess) which additionally contains 5–10% lactic acid as by-product.

Thus, the object of the present invention was a simple process for preparing (L)-2-chloropropionic acid and sodium (L)-2-chloropropionate of maximum chemical and optical purity (at least about 98% enantiomeric excess and less than 1% lactic acid).

Accordingly, a process for the preparation of (L)-2-chloropropionic acid and its alkali metal, alkaline earth metal or ammonium salts was found which comprises hydrolyzing isobutyl L-chloropropionate at a pH of from 4 to 8 in the presence of a lipase from Pseudomonas spec. DSM 8246*) and isolating the optically active reaction product from the reaction mixture either directly or after conversion of the salt into the acid in a conventional way, or further reacting it in situ. Pseudomonas sp. DSM 8246 was deposited with the DSM on Apr. 28, 1993, and was assigned the accession number DSM 8246 by this International Depository Authority.

*) DSM=Deutsche Sammlung von Mikroorganismen und Zellkulturen GmbH, Mascheroder Weg 1B, 38124 Braunschweig Isobutyl L-chloropropionate is advantageously prepared starting from D-lactic acid which can be prepared, for example, by a biotechnological process disclosed in EP-A 069 291. This entails a mixture of aqueous glucose solution, yeast autolysate, vitamins, catalytic amounts of phosphoric acid and a buffer for the lactic acid produced, e.g. calcium carbonate, being fermented at about 45° C. with the addition of lactic acid bacteria. The pH of the fermentation broth is preferably 4–6. A lactate is produced with evolution of carbon dioxide and is converted into D-lactic acid by adding an acid, preferably concentrated aqueous sulfuric acid. The D-lactic acid is subsequently extracted with isobutanol. The resulting D-lactic acid solution is then concentrated. Part of the lactic acid is esterified even during this. The remaining amount of lactic acid is esterified with acid catalysis, sulfuric acid being an example of a suitable acid (cf., for example, EP-A 287 426, DE-A 32 14 697 and DE-A 34 33 400). The water formed in the reaction is subsequently removed by distillation together with unreacted isobutanol.

The isobutyl D-lactate obtained can be chlorinated in a conventional way without further purification (cf., for example, EP-A 401 104, JP 61 057 534 (1986), JP 02 104 560 (1990), JP 61 068 445 (1986) and FR-A 24 59 221). The chlorination is preferably carried out with thionyl chloride in the presence of a catalyst, e.g. N,N-dimethylformamide, there being inversion at the asymmetric carbon atom. High boilers are removed from the crude product which is then purified by distillation.

It is possible in the manner described above to obtain isobutyl L-chloropropionate with a chemical purity of about 98–99%. The optical purity (L:D) is about 98–100%.

The lipase can be obtained from Pseudomonas spec. DSM 8246 by cultivating the bacterium in a nutrient medium and isolating the enzyme from the culture broth. Suitable nutrient media are those containing carbon sources, nitrogen sources, inorganic salts and, where appropriate, small amounts of trace elements and vitamins. Nitrogen sources which can be used are inorganic or organic nitrogen compounds or materials which contain these compounds. Examples are: ammonium salts, nitrates, corn steep liquor, yeast autolysate, yeast extract and hydrolyzed casein. Carbon sources which can be used are sugars such as glucose, polyols such as glycerol or else organic acids such as citric acid or fatty acids. Particularly suitable carbon sources are vegetable oils such as soybean oil, linseed oil or olive oil. Examples of inorganic salts are the salts of calcium, magnesium, manganese, potassium, zinc, copper, iron and other metals. Anions of these salts which should be particularly mentioned are phosphate and nitrate ions.

Preferred cultivation temperatures are 25° to 33° C. The pH of the medium is kept at 6 to 7.5, preferably at 6.5 to 7, during the fermentation using mineral acids such as 2N sulfuric acid or bases such as ammonia. The culture is carried out as submerged culture with vigorous aeration and stirring. Fermentation is continued until two consecutive measurements of enzyme activity at an interval of three hours show constant activity. An incubation time of from 40 to 60 hours is generally sufficient. It is possible in this way to obtain enzyme yields of 50 to 500 mg per 1 of culture broth.

The enzyme is isolated from the culture broth in a conventional way. In order to separate the microorganisms and insoluble material, the broth is centrifuged or filtered. The lipase is then obtained from the collected liquid phase either by precipitation with a water-miscible organic solvent, e.g. acetone or a lower alcohol, or by adding a salt, especially ammonium sulfate.

To increase the specific activity and to reduce further the content of impurities in the resulting crude lipase it is possible to redissolve and then reprecipitate it, for example by adding solvents or salt (fractional precipitation). However, the crude lipase can also be purified by crossflow filtrations of the enzyme-containing solution through suitable ultrafiltration membranes. In this method, low molecular weight impurities pass through the membrane while the enzyme is retained.

The particular advantage of the above process is that the lipase concentration in the resulting aqueous solution is very high. It is normally between about 5 and 30 g/l.

The lipase solution can be used directly for the present process. However, it is also possible to use the lipase immobilized on a solid carrier. Suitable solid carriers are the inert carrier materials customary for this purpose (cf., for example, Enzyme and Microbial Technology 14 (1992) 426).

The present process is advantageously carried out in a 2-phase system comprising aqueous enzyme solution and isobutyl L-chloropropionate which, together with the isobutanol produced in the reaction, forms the second phase.

It is also possible to add to the organic phase a solvent which is substantially immiscible with water, e.g. a hydrocarbon such as n-hexane, a chlorohydrocarbon or an ether.

The hydrolysis of isobutyl L-chloropropionate takes place in a pH range from about 4 to 8, preferably 5 to 7. The pH is normally adjusted before adding the lipase and is kept approximately constant during the reaction, normally by adding a base continuously or in portions. It is also possible, however, to use a suitable buffered system and to introduce the complete amount of base (e.g. sodium bicarbonate) at the outset.

Bases suitable for this purpose are, for example, alkali metal hydroxides such as sodium and potassium hydroxides, alkali metal and alkaline earth metal bicarbonates such as sodium bicarbonate, potassium bicarbonate and calcium bicarbonate, alkali metal and alkaline earth metal carbonates such as sodium carbonate, potassium carbonate and calcium carbonate, or tertiary amines such as triethylamine.

Since the preparation of the sodium salt of (L)-2-chloropropionic acid is preferred for reasons of cost, an appropriate sodium compound such as sodium hydroxide, sodium bicarbonate and sodium carbonate is used as base.

The reaction is generally carried out between 5° and 60° C., preferably between 20° and 40° C.

The reaction can be carried out under atmospheric pressure, under the autogenous pressure of the reaction mixture or under reduced pressure.

An embodiment which is particularly advantageous in respect of the progress of the reaction comprises continuous removal of the isobutanol formed during the reaction, preferably by distillation under reduced pressure.

The optically active reaction product can then be isolated from the reaction mixture in a conventional way or be reacted further in situ. Concerning further reaction, reference may be made for example to the statements in the publications GB-A 20 54 570, DE-A 30 24 265 and EP-A 009 285.

In order to isolate the optically active reaction product, the organic phase is separated off together with the lipase. Then the proportion of isobutanol which is dissolved in the aqueous phase is removed, expediently by distillation (e.g. at 50°–60° C. under 20–50 mbar). Experience has shown that the aqueous sodium (L)-2-chloropropionate solution then has a residual isobutanol content of less than 0.3% by weight. However, because it cannot be stored at 20°–25° C. for a lengthy period, it is advisable for the solution to be cooled until processed further or to be acidified and, if desired, worked up to (L)-2-chloropropionic acid. Concentrating the approximately 30% by weight aqueous sodium (L)-2-chloropropionate solution to 50–70% by weight followed by cooling to −20° to −50° C. results, for example, in a suspension of crystals which is stable for several weeks.

The sodium (L)-2-chloropropionate can be isolated in a conventional way, e.g. by the abovementioned low-temperature crystallization, but also spray- or freeze-drying. In the case of spray-drying, for example with an inlet temperature of 200° C. and an outlet temperature of the solid of 80°–90° C., the sodium (L)-2-chloropropionate is obtained in the form of a dry, free-flowing powder with a residual water content of from 0.2 to 0.7%. The optical activity is completely retained in any event.

Acidification of the aqueous sodium (L)-2-chloropropionate solution, e.g. with sulfuric acid, to a pH below 2 results in free (L)-2-chloropropionic acid. The latter can be extracted from the aqueous phase using suitable organic solvents in which 2-chloropropionic acid dissolves well and which have only low miscibility with water. Suitable for this purpose are, for example, ethers such as methyl tert-butyl ether or chlorinated hydrocarbons such as dichloromethane and 1,2-dichloroethane.

After removal of the organic solvent, the (L)-2-chloropropionic acid can then be purified in a conventional way, expediently by distillation under reduced pressure (for example the distillate temperature is about 80° C. under 12 mbar).

(L)-2-Chloropropionates and (L)-2-chloropropionic acid are important intermediates for crop protection agents and drugs. They are particularly suitable for preparing D-2-phenoxypropionic acid (cf., for example, DE-A 15 43 841) which can be converted into R-2-(4-hydroxyphenoxy)propionic acid in a biotechnological process (cf. in this connection, for example, WO 90/11362 and EP-A 465 494). R-2-(4-Hydroxyphenoxy)propionic acid is eventually used as starting material for the preparation of aryloxyphenoxypropionic acid derivatives with herbicidal activity.

PREPARATION EXAMPLES

Example 1

Preparation and purification of the lipase from Pseudomonas spec. DSM 8246

The following medium was used to cultivate the microorganism Pseudomonas spec. DSM 8246:

| | |
|---|---|
| $KH_2PO_4$ | 20 g/l |
| $Na_2HPO_4$ | 10 g/l |
| $MgSO_4$ | 5 g/l |
| $CaCl_2 \times 2H_2O$ | 3 g/l |
| $FeSO_4 \times 7H_2O$ | 0.5 g/l |
| $MnSO_4 \times 4H_2O$ | 0.005 g/l |
| $CoCl_2 \times 6H_2O$ | 0.005 g/l |
| $CuSO_4 \times 5H_2O$ | 0.005 g/l |
| $ZnSO_4 \times 7H_2O$ | 0.005 g/l |
| Yeast extract | 5 g/l |

The carbon source used was refined soybean oil which was pumped in at a constant rate of 1 g/l×h. The pH was kept constant at pH 6.5 throughout the fermentation using 2N $H_2SO_4$ and 25% strength $NH_4OH$.

The seed culture was obtained by inoculating 400 ml of nutrient broth medium pH 6.5 with the microorganism Pseudomonas spec. DSM 8246.

The seed culture was incubated on a shaker at 30° C. for 10 h.

The medium was inoculated at 30° C. and pH 6.5 with 5 parts by volume of the seed culture per 100 parts by volume of medium. The main cultivation was carried out at 30° C.

in 10 l stirred fermenters with a content of 8 l. The stirring speed of the inbuilt paddle stirrers was 1000 revolutions per minute, and the aeration rate was one volume of air per minute and volume of fermentation broth. After 60 h, the fermentation broth showed a constant activity in two consecutive activity measurements of 300 F.I.P. (=Federation International Pharmaceutique) enzyme units per ml (for the method, see, for example, R. Ruyssen and A. Lauwers, Pharmaceutical Enzymes, E. Story-Scientia P.V.B.A., Scientific Publishing Company, Gent/Belgium, 1978, pages 78–82).

The fermentation was then stopped and the lipase which was produced was isolated from the fermentation broth in the following way:

The discharge from the fermenter was diluted with n-propanol to 65% by volume alcohol. The biomass and precipitated by-products were removed by centrifugation. The clear, alcoholic enzyme solution was concentrated under reduced pressure to one third of the initial volume. Although this enzyme solution was already suitable for the hydrolysis of isobutyl L-chloropropionate, it was washed with three volumes of water in a diafiltration unit (cellulose triacetate crossflow filtration units, separation limit 20,000 nominal molecular weight, from Sartorius, Göttingen) to increase the activity further and then concentrated to one quarter of the initial volume by filtration. The lipase was precipitated from this enzyme concentrate by adding n-propanol to a content of 85% by volume. The precipitate containing the lipase activity was harvested by centrifugation and taken up in an aqueous solution containing 65 parts by volume of n-propanol. The ratio by weight of precipitate to n-propanol/water mixture was 1 to 10.

Undissolved precipitate was removed by centrifugation. The lipase was precipitated from the clear supernatant from the centrifugation by increasing the n-propanol content to 80 parts by volume. The precipitate was harvested by centrifugation and was freeze-dried. The enzyme powder obtained in this way had a specific activity of 7100 F.I.P. enzyme units per milligram of protein.

Example 2
Hydrolysis of isobutyl L-chloropropionate using lipase (according to the invention)

A suspension of 200 g of isobutyl L-chloropropionate in 400 g of water was vigorously stirred at 20°–25° C. and neutralized with 25% by weight aqueous sodium hydroxide solution (pH=7.5). Then 500 mg of lipase (from Pseudomonas spec. DSM 8246; activity about 400 U/mg) were added and the pH of the reaction mixture was kept constant at 7.5 by continuous addition of 10 normal aqueous sodium hydroxide solution. After 6¼ h, 97.3% of the theoretically required amount of sodium hydroxide solution had been consumed. In order to stop the reaction, the isobutanol phase was removed together with the lipase. Freeze-drying of the aqueous phase resulted in sodium (L)-2-chloropropionate with an enantiomeric purity of 99.2%. Yield: 95.8%. The contamination with lactic acid was below 0.05%.

Example 3
Hydrolysis of isobutyl L-chloropropionate using immobilized lipase (according to the invention):

A suspension of 1000 g (6.08 mol) of isobutyl L-chloropropionate in 2000 g of water was vigorously stirred at 20°–25° C. and 25% by weight aqueous sodium hydroxide solution was added until the pH was 5–6. Then 2.5 g of lipase (activity about 400 U/mg; from Pseudomonas spec. DSM 8246; lipase immobilized on "Accurel® EP100" polypropylene powder from Akzo, particle size 200–1000μ) were added, keeping the pH of the reaction mixture constant (between 5 and 6) by continuous addition of 25% by weight sodium hydroxide solution. After 98% of the theoretically required amount of sodium hydroxide solution had been consumed (after about 18 h), the lipase was filtered off. The organic phase of the filtrate was separated off. Isobutanol dissolved in the aqueous phase was removed by distillation as azeotrope with water at 60° C. under 50 mbar in a thin-film evaporator. 2340 g of an approximately 30% by weight solution of sodium L-chloropropionate in water were obtained (yield: about 88%).

450 g of this solution were acidified to a pH of about 1 with about 60 g of concentrated sulfuric acid. After addition of about 200 ml of methyl tert-butyl ether the organic phase was separated off. The aqueous phase was extracted three times with 200 ml of methyl tert-butyl ether each time. The combined organic phases were dried over sodium sulfate and concentrated at 300 mbar/50° C., after which the residue was distilled through a 30 cm Vigreux column. 84 g of L-chloropropionic acid were obtained as a colorless liquid of boiling point 82° C./13 mbar with a chemical purity of more than 99% and an optical purity of L:D=99:1.

1500 g of the above solution of sodium L-chloropropionate in water were spray-dried in a tower with an inlet temperature of 200° C. At an outlet temperature of 83° C., 480 g of solid sodium L-chloropropionate were obtained as a white powder with a residual water content of 0.4% and an optical purity of 99:1 (L:D).

Example 4
Hydrolysis of isobutyl L-chloropropionate using lipase with continuous removal of isobutanol (according to the invention)

A mixture of 164.5 g (1.0 mol) of isobutyl L-chloropropionate and 330 g of water was stirred at 35°–40° C. while 25% by weight aqueous sodium hydroxide solution was added until the pH was 5–6. 5.0 ml of an approximately 5% by weight lipase solution (activity about 100,000 U/ml) were then added to the mixture. The reaction took place at 35°–40° C. while keeping the pH of the reaction mixture at 5–6 by metering in 25% by weight sodium hydroxide solution. After about 20% of the calculated amount of sodium hydroxide solution had been consumed, the pressure was slowly reduced to 80 mbar, until the reaction mixture boiled. The colorless distillate with a boiling point of 37° C. under 80 mbar comprised water, isobutanol and small amounts of isobutyl L-chloropropionate*). Complete conversion of the initial ester (after about 2 hours) was evident from a large rise in the pH of the reaction mixture after each further drop of sodium hydroxide solution. Addition of sodium hydroxide solution was then stopped immediately. The mixture was then stirred for a few minutes until the pH had returned to about 6. 507 g of a 23% strength sodium L-2-chloropropionate solution containing less than 0.5% isobutanol and not more than 0.05% isobutyl L-chloropropionate were obtained. Yield: 89% (based on isobutyl L-chloropropionate employed).

*) 2 phases: 39 g of an aqueous phase comprising 88% water and 12% isobutanol; 73 g of an organic phase comprising 76% isobutanol, 12% isobutyl L-chloropropionate and 12% water Example 5 (=Comparative example)
Hydrolysis of isobutyl (L)-2-chloropropionate with sodium hydroxide solution (without lipase)

2467 g (15 mol) of IB-L-C (enantiomeric purity at least 99%) and 1.6 l of water were placed in a 6 l jacketed reaction vessel and stirred. The resulting suspension had a pH of about 2 and, at 40°–45° C., a total of 1200 g (15 mol) of 50% by weight aqueous sodium hydroxide solution was added. The addition took place in accordance with the consumption of sodium hydroxide solution so that the pH remained constant at 12.3. After the addition was complete (about 2 hours) the reaction mixture was neutralized (pH=7–8) with 20% by weight hydrochloric acid. An azeotrope of isobutanol and water was then removed by distillation at about 40° C. under 60 mbar, approximately 500 ml of water being additionally introduced into the distillation vessel during the distillation. After about 100 min, about 2000 g of azeotrope had distilled out. The residue was worked up to the product in a conventional way. Yield: about 96%; optical purity: 95.5:4.5 (L:D).

We claim:

1. A process for the preparation of (L)-2-chloropropionic acid or its alkali metal salt, alkaline earth metal salt or ammonium salt which comprises hydrolyzing isobutyl (L)-2-chloropropionate at a pH of from 4 to 8 with a lipase from Pseudomonas spec. DSM 8246 and isolating (L)-2-chloropropionic acid or its salt from the reaction mixture consisting of an organic phase and an aqueous phase either directly or after conversion of the salt into the acid in a conventional way, or further reacting the (L)-2-chloropropionic acid or its salt in situ.

2. The process as claimed in claim 1, wherein the reaction is carried out at from 5° to 60° C.

3. The process as claimed in claim 1, wherein the pH range is kept constant during the reaction by adding a base.

4. The process as claimed in claim 1, wherein the reaction is carried out with continuous removal of the isobutanol produced thereby.

5. The process as claimed in claim 1, wherein the lipase is immobilized on a solid carrier.

6. The process according to claim 1, wherein (L)-2-chloropropionic acid or its salt is isolated from the reaction mixture by a) removing the lipase and the organic phase, b) removing dissolved isobutanol from the aqueous phase and c) isolating the (L)-2-chloropropionic acid by transferring it into an inert organic solvent and isolating it therefrom.

* * * * *